United States Patent [19]
Geerlings et al.

[11] Patent Number: 5,981,608
[45] Date of Patent: Nov. 9, 1999

[54] CATALYST AND PROCESS FOR THE PREPARATION OF HYDROCARBONS

[75] Inventors: Jacobus Johannes Cornelis Geerlings; Marinus Franciscus Goes; Hans Michiel Huisman; Jean-Paul Lange; Heiko Oosterbeek; Paulus Johannes Maria Rek; David Schaddenhorst, all of Amsterdam, Netherlands

[73] Assignee: Shell Oil Company, Houston, Tex.

[21] Appl. No.: 09/123,711

[22] Filed: Jul. 28, 1998

Related U.S. Application Data

[62] Division of application No. 08/664,467, Jun. 17, 1996.

[30] Foreign Application Priority Data

Jun. 16, 1995 [EP] European Pat. Off. .............. 95201644

[51] Int. Cl.$^6$ ............................ C07C 27/00; B01J 21/08; B01J 23/00; B01J 23/32; B01J 23/40
[52] U.S. Cl. ......................... 518/715; 518/700; 502/241; 502/311; 502/312; 502/324; 502/326; 502/439
[58] Field of Search ..................................... 502/324, 326, 502/311, 312, 241, 439; 518/700, 715

[56] References Cited

U.S. PATENT DOCUMENTS

| | | | |
|---|---|---|---|
| 4,588,708 | 5/1986 | Klabunde et al. ....................... | 502/241 |
| 5,320,999 | 6/1994 | Muramatsu et al. ..................... | 502/303 |

*Primary Examiner*—Paul J. Killos
*Assistant Examiner*—J. Parsa

[57] ABSTRACT

The present invention relates to a catalyst for use in a process for the preparation of hydrocarbons comprising cobalt and manganese and/or vanadium, supported on a carrier, wherein the cobalt:(manganese+vanadium) atomic ratio is at least 12:1. Preferably, the cobalt:(manganese+vanadium) atomic ratio is at most 1500:1. The invention further relates to a process for the preparation of hydrocarbons which comprises contacting a mixture of hydrogen and carbon monoxide at elevated temperature and pressure with a catalyst as described hereinbefore. Typically, at least part of the cobalt is present in the metallic state.

6 Claims, No Drawings

CATALYST AND PROCESS FOR THE PREPARATION OF HYDROCARBONS

This is a division of application Ser. No. 08/664,467 filed Jun. 17, 1996, the entire disclosure of which is hereby incorporated by reference.

BACKGROUND OF THE INVENTION

The present invention relates to a catalyst and process for the preparation of hydrocarbons from synthesis gas, that is a mixture of carbon monoxide and hydrogen.

The preparation of hydrocarbons from synthesis gas is well known in the art and is commonly referred to as Fischer-Tropsch synthesis.

Catalysts suitable for use in a Fischer-Tropsch synthesis process typically contain a catalytically active metal of Group VIII of the Periodic Table of the Elements (Handbook of Chemistry and Physics, 68th edition, CRC Press, 1987–1988). In particular, iron, nickel, cobalt and ruthenium are well known catalytically active metals for such catalyst. Cobalt has been found to be most suitable for catalyzing a process in which synthesis gas is converted to primarily paraffinic hydrocarbons containing 5 or more carbon atoms. In other words, the $C_{5+}$ selectivity of the catalyst is high.

Much research effort has been directed to finding catalysts having a higher $C_{5+}$ selectivity than known catalysts at the same or higher activity.

Thus, European patent specification No. 398 420 describes that the $C_{5+}$ selectivity of catalysts comprising cobalt and zirconium, titanium or chromium on a porous carrier, having a small external surface area, can be improved by contacting the catalyst with a synthesis gas having a low hydrogen to carbon monoxide ratio, typically, from 1.1 to 1.2.

European patent specification No. 178 008 discloses cobalt catalysts supported on a porous carrier, wherein most cobalt is concentrated in the peel of the catalyst particle.

European patent specification No. 167 215 discloses a cobalt/zirconia on silica catalyst for use in a fixed catalyst bed which catalyst satisfies a relation between the internal surface area and the external surface area.

European patent specification No. 168 894 discloses an optimal activation procedure to increase the $C_{5+}$ selectivity of a cobalt-based Fischer-Tropsch catalyst.

European patent specification No. 363 537 describes an increase in activity of cobalt catalysts supported on titania, by adding up to 15% by weight of silica to the titania carrier.

European patent application publication No. 498 976 describes catalysts containing cobalt and rhenium supported on a titania carrier. It is claimed that these catalysts have a high volumetric productivity (activity).

Despite the research effort in this field there is still room for improvement. Accordingly, it would be desirable if a catalyst could be found which has an even higher $C_{5+}$ selectivity at the same or, preferably, higher activity than known catalysts. In particular, it would be desirable if a catalyst could be found having a high $C_{5+}$ selectivity and activity when contacted with a synthesis gas feed having a high hydrogen to carbon monoxide ratio, typically in the range from 1.5 to 2.5.

It has now surprisingly been found that a catalyst comprising as catalytically active compounds cobalt and a small amount of manganese and/or vanadium, typically comprising a cobalt:(manganese+vanadium) atomic ratio of at least 12:1, exhibits a higher $C_{5+}$ selectivity and a higher activity when used in a process for the preparation of hydrocarbons, compared to catalysts which are otherwise the same but containing cobalt only, or containing a relatively higher amount of manganese and/or vanadium.

SUMMARY OF THE INVENTION

The present invention relates to a catalyst comprising cobalt and manganese and/or vanadium, supported on a carrier, wherein the cobalt:(manganese+vanadium) atomic ratio is at least 12:1. The present invention also relates to a process for the preparation of the subject catalyst which includes impregnating the carrier with a solution of cobalt salt and a solution of manganese and/or vanadium salt, drying, and optionally calcining. The present invention further relates to a process for the preparation of hydrocarbons utilizing a catalyst of the invention.

DETAILED DESCRIPTION OF THE PREFERRED EMBODIMENTS

The fact that a small amount of manganese and/or vanadium is capable of promoting the $C_{5+}$ selectivity and activity properties of a cobalt-containing catalyst is highly surprising as those elements, especially manganese, are known to act as a promoter for the preparation of olefinic hydrocarbons containing 2–6 carbon atoms, whilst normally decreasing the $C_{5+}$ selectivity of cobalt-containing catalysts.

European patent application publication No. 71 770 describes a process for the preparation of linear a-olefins from synthesis gas. Inter alia cobalt/manganese and cobalt/vanadium catalysts are claimed to be applicable in this process. The $C_{5+}$ selectivity of a catalyst comprising cobalt and manganese in a ratio of 1:6, is only 50%.

Van der Riet et al. (1986) J. Chem. Soc., Chem. Commun., pages 798–799 describe selective formation of $C_3$ hydrocarbons from carbon monoxide and hydrogen using cobalt-manganese oxide catalysts. The cobalt/manganese ratio is typically 1:1.

International PCT patent application WO 93/05000 describes a Fischer-Tropsch catalyst comprising cobalt and scandium. Optionally, the catalyst contains additional promoters like thoria and/or other materials such as magnesia and manganese.

"The Fischer-Tropsch and Related Synthesis" by H. H. Storch, N. Golumbic, and R. B. Anderson (John Wiley and Sons, New York, 1951), referred to in International PCT application WO 93/05000, provides a review of early work on Fischer-Tropsch catalysts, including catalysts comprising cobalt and manganese and/or vanadium. On page 120 reference is made to experiments in which it was found that cobalt-vanadium oxide and cobalt-manganese oxide catalysts were inactive as Fischer-Tropsch catalysts. However, on page 198 reference is made to experiments in which it was found that a catalyst containing cobalt and manganese in an atomic ratio of 6.2:1 had a higher $C_{5+}$ selectivity as compared to a catalyst containing cobalt and thoria, but at a significantly lower synthesis gas conversion.

Australian patent application No. 46119/85 describes a catalyst containing cobalt, silica and a base or alkaline material, typically an alkali or alkaline earth metal. Optionally additional promoters may be present chosen from salts of elements chosen from the group of aluminum, magnesium, zinc, copper, manganese, chromium, vanadium, germanium, boron, molybdenum, lanthanum, the Rare Earths and the like or combinations thereof and arsenic or antimony. It is claimed that these catalysts have a high selectivity towards lower boiling 1-alkenes.

Typically, the catalysts according to the present invention do not contain alkali or alkaline earth metals, apart from possible impurities introduced with starting materials in the preparation process of the catalysts of the present invention. Typically, the atomic ratio of alkali or alkaline earth metals to cobalt metal is less than 0.01, preferably, less than 0.005.

U.S. Pat. No. 4,588,708 discloses cobalt and manganese containing catalysts for use in isomerization and hydrogenation of olefins and hydrogenolysis. The cobalt/manganese atomic ratio may vary between wide limits. In one Example a catalyst has been disclosed, containing cobalt and manganese in an atomic ratio of 39:1, on a silica support.

Therefore, according to the present invention there is provided a catalyst comprising cobalt and manganese and/or vanadium, supported on a carrier, wherein the cobalt:(manganese+vanadium) atomic ratio is at least 12:1, with the proviso that the catalyst does not contain cobalt and manganese in an atomic ratio of 39:1 on a silica support.

According to another aspect, the catalyst comprises cobalt and manganese and/or vanadium, supported on a carrier, wherein the cobalt:(manganese+vanadium) atomic ratio is at least 12:1, and wherein the carrier comprises titania, zirconia or mixtures thereof.

The catalyst preferably comprises cobalt and manganese, wherein the cobalt:manganese atomic ratio is at least 12:1.

Preferably, the cobalt:(manganese+vanadium) atomic ratio is at most 1500:1; more preferably at most 500:1; still more preferably at most 100:1; most preferably at most 38:1.

The cobalt:(manganese+vanadium) atomic ratio is preferably at least 15:1; more preferably at least 16:1; still more preferably at least 18:1.

It will be appreciated by those skilled in the art that in principle catalysts can be produced which contain manganese and/or vanadium in catalytically active amounts falling within the ranges given above, but which catalysts in addition contain other manganese and/or vanadium components which are catalytically less active or inactive. It will be appreciated that also these catalysts are within the gist of the invention, which is that small amounts of catalytically active manganese and/or vanadium are capable of enhancing the $C_{5+}$ selectivity of cobalt-containing catalysts, when used in a process for the preparation of hydrocarbons from synthesis gas.

Therefore, in a further aspect, the present invention relates to a catalyst comprising cobalt and manganese and/or vanadium, having a $C_{5+}$ selectivity which is at least 0.5% higher, preferably at least 1% higher, than a reference catalyst comprising no manganese and/or vanadium, when tested in a process for the preparation of hydrocarbons, under such conditions that the activity of both catalysts is the same, at a pressure of 26 bar abs., a $H_2/CO$ molar ratio of 2, and a GHSV of 800 $h^{-1}$.

It will be understood that the reference catalyst should have the same total metal loading as the catalyst according to the present invention, and any carrier, if present, should be the same.

In a preferred embodiment, the catalyst according to the present invention further comprises a carrier, usually a refractory oxide carrier. Examples of suitable refractory oxide carriers include alumina, silica, titania, zirconia, or mixtures thereof, such as silica-alumina or physical mixtures such as silica and titania. Preferably, the carrier comprises titania, zirconia, or mixtures thereof.

According to a preferred embodiment, the carrier comprising titania, zirconia, or mixtures thereof, may further comprise up to 50% by weight of another refractory oxide, typically silica or alumina. More preferably, the additional refractory oxide, if present, comprises up to 20% by weight, even more preferably up to 10% by weight, of the carrier.

The carrier most preferably comprises titania, in particular titania which has been prepared in the absence of sulfur-containing compounds. An example of such preparation method involves flame hydrolysis of titanium tetrachloride. It will be appreciated that the titania powder derived from such preparation method may not be of the desired size and shape. Thus, usually a shaping step is required to prepare the carrier. Shaping techniques are well known to those skilled in the art and include palletizing, extrusion, spray-drying, and hot oil dropping methods. It may be desirable and advantageous to use titania in which the anatase:rutile weight ratio is at most 2:3; preferably, at most 1:10. If such a titania is used, it is more preferable to employ a titania of the rutile variety. Alternatively, it may be desirable and advantageous to use titania having a relatively low surface area, typically in the range from 0.5 to 80 $m^2/g$, preferably from 0.5 to 50 $m^2/g$.

The amount of cobalt present in the catalyst may vary widely. Typically, the catalyst comprises 1–100 parts by weight of cobalt per 100 parts by weight of carrier, preferably, 3–60 parts by weight, more preferably, 5–40 parts by weight.

In addition to manganese and/or vanadium, the catalyst may comprise one or more additional promoters known to those skilled in the art. Preferably any additional promoters are selected from Group IIIB, IVB, the noble metals of Group VIII of the Periodic Table or rhenium, niobium or tantalum, more preferably from Group IVB, the noble metals of Group VIII of the Periodic Table or rhenium, niobium or tantalum. Especially preferred additional promoters include zirconium, titanium, ruthenium, platinum, palladium and/or rhenium. The amount of additional promoter, if present, is typically between 0.1 and 150 parts by weight, for example between 1 and 150 parts by weight, per 100 parts by weight of the carrier.

The catalyst according to the present invention may suitably be prepared by methods known to those skilled in the art, such as by precipitating the catalytically active compounds or precursors onto a carrier; spray-coating, kneading and/or impregnating the catalytically active compounds or precursors onto a carrier; spray-coating, kneading and/or impregnating the catalytically active compounds or precursors onto a carrier; and/or extruding one or more catalytically active compounds or precursors together with carrier material to prepare catalyst extrudates.

It will be appreciated by those skilled in the art that the most preferred method of preparation may vary, depending, e.g., on the desired size of the catalyst particles. It belongs to the skill of the skilled person to select the most suitable method for a given set of circumstances and requirements.

A preferred method of preparing the catalyst according to the present invention is by impregnating the catalytically active compounds or precursors onto a carrier. Thus, typically, the carrier is impregnated with a solution of a cobalt salt and a solution of a manganese and/or vanadium salt. Preferably, the carrier is impregnated simultaneously with the respective metal salts. Thus, according to a preferred embodiment, the process for preparing the catalyst according to the present invention comprises co-impregnating the carrier with a solution of a cobalt salt and a manganese and/or vanadium salt. In case a cobalt and manganese containing catalyst is to be prepared, most preferably a highly concentrated solution is employed. A suitable method to arrive at such a concentrated solution is to use a mixture of molten cobalt nitrate and manganese nitrate salts.

The impregnation treatment is typically followed by drying and, optionally, calcining. Drying is typically carried out at a temperature of 50 to 300° C. for up to 24 hours, preferably, 1 to 4 hours.

Calcination is typically carried out at a temperature between 200 and 900° C., preferably, between 250 and 600° C. The duration of the calcination treatment is typically from 0.5 to 24 hours, preferably from 1 to 4 hours. Suitably, the calcination treatment is carried out in an oxygen-containing atmosphere, preferably air. It will be appreciated that the average temperature during the calcination treatment will normally be higher than the average temperature during the drying treatment.

The catalyst according to the present invention is typically used to catalyze a process for the preparation of hydrocarbons from synthesis gas. Typically, when in use in that process, at least part of the cobalt is present in its metallic state. Following the calcination treatment, however, much of the cobalt in the catalyst will be in an oxidized state.

Therefore, it is normally advantageous to activate the catalyst prior to use by a reduction treatment, in the presence of hydrogen at elevated temperature. Typically, the reduction treatment involves treating the catalyst at a temperature in the range from 100 to 450° C. for 1 to 48 hours at elevated pressure, typically from 1 to 200 bar abs. Pure hydrogen may be used in the reduction treatment, but it is preferred to apply a mixture of hydrogen and an inert gas, like nitrogen. The relative amount of hydrogen present in the mixture may range between 0 and 100% by volume.

According to one preferred embodiment, the catalyst is brought to the desired temperature and pressure levels in a nitrogen gas atmosphere. Subsequently, the catalyst is contacted with a gas mixture containing only a small amount of hydrogen gas, the rest being nitrogen gas. During the reduction treatment, the relative amount of hydrogen gas in the gas mixture is gradually increased up to 50% or even 100% by volume.

If possible, it is preferred to activate the catalyst in-situ, that is inside the reactor. European patent application No. 95203040.1 describes an in-situ catalyst activation process which comprises contacting the catalyst in the presence of hydrocarbon liquid with a hydrogen-containing gas at a hydrogen partial pressure of at least 15 bar abs., preferably at least 20 bar abs., more preferably at least 30 bar abs. Typically, in this process the hydrogen partial pressure is at most 200 bar abs.

In a further aspect, the present invention relates to a process for the preparation of hydrocarbons, which comprises contacting a mixture of carbon monoxide and hydrogen at elevated temperature and pressure with a catalyst as described hereinbefore, typically comprising cobalt and manganese and/or vanadium, wherein the cobalt: (manganese+vanadium) atomic ratio is at least 11:1.

The process is typically carried out at a temperature in the range from 125 to 350° C., preferably 175 to 275° C. The pressure is typically in the range from 5 to 150 bar abs., preferably from 5 to 80 bar abs., in particular from 5 to 50 bar abs.

Hydrogen and carbon monoxide (synthesis gas) is typically fed to the process at an atomic ratio in the range from 1 to 2.5. It is known that especially low hydrogen to carbon monoxide molar ratios will increase the $C_{5+}$ selectivity of Fischer-Tropsch catalysts. However, as the ratio in which the synthesis gas is normally consumed is about 2, expensive recycles have to be applied if synthesis gas having a low hydrogen to carbon monoxide molar ratio is fed to the process. It has now most surprisingly been found that the $C_{5+}$ selectivity of the catalyst according to the present invention is remarkably high, even when using synthesis gas having a high hydrogen to carbon monoxide molar ratio. In a preferred embodiment of the hydrocarbon synthesis process of the present invention, the hydrogen to carbon monoxide atomic ratio is in the range from 1.5 to 2.5.

The gas hourly space velocity may vary within wide ranges and is typically in the range from 400 to 10000 Nl/l/h, for example from 400 to 4000 $h^{-1}$.

The process for the preparation of hydrocarbons may be conducted using a variety of reactor types and reaction regimes, for example a fixed bed regime, a slurry phase regime or an ebullating bed regime. It will be appreciated that the size of the catalyst particles may vary depending on the reaction regime they are intended for. It belongs to the skill of the skilled person to select the most appropriate catalyst particle size for a given reaction regime.

Further, it will be understood that the skilled person is capable to select the most appropriate conditions for a specific reactor configuration and reaction regime. For example, the preferred gas hourly space velocity may depend upon the type of reaction regime that is being applied. Thus, if it is desired to operate the hydrocarbon synthesis process with a fixed bed regime, preferably the gas hourly space velocity is chosen in the range from 500 to 2500 Nl/l/h. If it is desired to operate the hydrocarbon synthesis process with a slurry phase regime, preferably the gas hourly space velocity is chosen in the range from 1500 to 7500 Nl/l/h.

The invention will now be illustrated further by means of the following Examples.

EXAMPLE I (Comparative)

Commercially available titania particles (30–80 MESH) of the rutile variety were impregnated with a concentrated cobalt nitrate solution.

The solution was prepared by heating solid cobalt nitrate ($Co(NO_3)_2 6H_2O$) to a temperature of 60° C., thus causing the cobalt nitrate to dissolve in its own crystal water. The impregnated titania particles were dried for 2 hours at 120° C. and subsequently calcined in air for 4 hours at 400° C. The catalyst (I) thus produced contained 10% by weight of cobalt compounds, expressed as cobalt metal.

EXAMPLE II

The procedure of Example I was repeated but now the impregnating solution contained in addition manganese nitrate. The solution was prepared in the same way as outlined in Example I, but part of the solid cobalt nitrate was replaced by manganese nitrate ($Mn(NO_3)_2 4H_2O$).

The catalyst (II) contained 10% by weight of metal compounds, expressed as metal. The cobalt:manganese atomic ratio amounted to 20:1.

EXAMPLE III (Comparative)

The procedure of Example II was repeated, but the impregnating solution contained more manganese nitrate.

The catalyst (III) contained 10% by weight of metal compounds, expressed as metal. The cobalt:manganese atomic ratio amounted to 10:1.

EXAMPLE IV

Catalysts I, II and III were tested in a process for the preparation of hydrocarbons. Microflow reactors A, B and C, containing 10 grammes of catalysts I, II and III respectively, were heated to a temperature of 260° C., and pressurized with a continuous flow of nitrogen gas to a pressure of 2 bar abs. The catalysts were reduced in-situ for 24 hours with a mixture of nitrogen and hydrogen gas. During reduction, the relative amount of hydrogen in the mixture was gradually increased from 0% to 100%. The water concentration in the off-gas was kept below 3000 ppmv.

Following reduction, the pressure was increased to 26 bar abs. The reaction was carried out with a mixture of hydrogen and carbon monoxide at a $H_2/CO$ atomic ratio of 2:1. The GHSV amounted to 800 Nl/l/h.

The space time yield (STY), expressed as grammes hydrocarbon product per liter catalyst per hour, and the $C_{5+}$ selectivity, expressed as a weight percentage of the total hydrocarbon product, were determined for each of the reactors after 100 hours of operation.

The results are set out in Table I.

TABLE I

| | Reactor: | | |
|---|---|---|---|
| | A | B | C |
| | | Catalyst: | |
| | I (no Mn) | II (Co/Mn = 20) | III (Co/Mn = 10) |
| STY (g/l/h): | 70 | 100 | 65 |
| C5 + select. (%): | 89 | 91 | 87 |

It will be appreciated that both the activity and the selectivity of catalyst II, according to the invention, is much better than the activity and selectivity of catalysts I and III, not according to the invention.

Accordingly, in a further aspect, the invention relates to the use of manganese and/or vanadium for the purpose of increasing the activity and/or $C_{5+}$ selectivity of a cobalt-containing catalyst in a process for the preparation of hydrocarbons.

What is claimed is:

1. A process for the preparation of hydrocarbons, comprising contacting a mixture of carbon monoxide and hydrogen at elevated temperature and pressure with a catalyst comprising cobalt and manganese, or cobalt and vanadium, or cobalt and manganese and vanadium supported on a carrier selected from the group consisting of alumina, silica, titania, zirconia, and mixtures thereof, wherein the cobalt:(manganese+vanadium) atomic ratio is at least 12:1 and at most 1500:1, with the proviso that the catalyst does not contain cobalt and manganese in the form of a solvated dispersion in an atomic ratio of 39:1, and wherein at least part of the cobalt is in the metallic state.

2. The process according to claim 1, wherein the temperature is in the range from 125 to 350° C.

3. The process according to claim 1, wherein the pressure is in the range from 5 to 50 bar abs.

4. The process according to claim 1, wherein the hydrogen to carbon monoxide molar ratio is in the range from 1 to 2.5.

5. The process according to claim 4, wherein the hydrogen to carbon monoxide molar ratio is in the range from 1.5 to 2.5.

6. The process according to claim 1, wherein the gas hourly space velocity is in the range from 400 to 4000 $h^{-1}$.

* * * * *